US005422106A

United States Patent [19]

Lambert et al.

[11] Patent Number: 5,422,106
[45] Date of Patent: Jun. 6, 1995

[54] **METHOD OF CONTROLLING COLEOTERA USING *BACILLUS THURINGIENSIS* STRAINS** MG P-14025 AND LMG P-14026

[75] Inventors: Bart J. Lambert, Beernem; Stefan K. Jansens; Marnix Peferoen, both of Ghent, all of Belgium

[73] Assignee: Plant Genetic Systems, N.V., Brussels, Belgium

[21] Appl. No.: 306,943

[22] Filed: Sep. 16, 1994

Related U.S. Application Data

[62] Division of Ser. No. 89,809, Jul. 12, 1993, Pat. No. 5,369,027.

[51] Int. Cl.[6] ........................ C12N 1/20; A01N 63/02

[52] U.S. Cl. ............................ 424/93.461; 435/252.5; 435/832

[58] Field of Search ................ 424/93.461; 435/252.5, 435/832

[56] References Cited

U.S. PATENT DOCUMENTS

| | | | |
|---|---|---|---|
| 4,797,276 | 1/1989 | Herrnstadt et al. | 435/68 |
| 5,187,091 | 2/1993 | Donovan et al. | 435/240.4 |
| 5,208,017 | 5/1993 | Bradfisch et al. | 435/242 |

FOREIGN PATENT DOCUMENTS

| | | |
|---|---|---|
| 0318143 | 5/1989 | European Pat. Off. . |
| 0324254 | 7/1989 | European Pat. Off. . |
| 90/13651 | 11/1990 | WIPO . |
| 91/14778 | 10/1991 | WIPO . |
| 92/13954 | 8/1992 | WIPO . |

OTHER PUBLICATIONS

Timothy B. Johnson, et al; "Insecticidal Activity of EG4961, a Novel Strain of *Bacillus thuringiensis* Toxic to Larvae and Adults of Southern corn Rootworm (Coleoptera: Chrysomelidae) and Colorado Potato Beetle (Coleoptera: Chrysomelidae)", *Journal of Economic Entomology;* vol. 86, No. 2; pp. 330–333; Apr. 1993.

Annette C. Slaney, et al; "Mode of Action of *Bacillus Thuringiensis* Toxin CryIIIA: An Analysis of Toxicity in *Leptinotarsa decemlineata* (Say) And *Diabrotica undecimpunctata Howardi* Barber"; *Insect Biochem. Molec. Biol.;* vol. 22, No. 1; pp. 9–18; 1992.icide; 1993.

Ravi Tailor, et al; "Identification and Characterization of a Novel *Bacillus thuringiensis* δ-endotoxin Entomocidal to Coleopteran and Lepidopteran Larvae"; *Molecular Microbiology,* vol. 6, No. 9; pp. 1211–1217; 1992.

*Primary Examiner*—David M. Naff
*Assistant Examiner*—L. Blaine Lankford
*Attorney, Agent, or Firm*—Burns, Doane, Swecker & Mathis

[57] ABSTRACT

Two new *Bacillus thuringienses* strains, LMG P-14025 and LMG P-14026, produce insecticidal components that are toxic to Coleoptera, more particularly toxic to *Diabrotica spp.* The strains themselves, their sporulated cultures, or their insecticidally effective components can be used as the active ingredient in an insecticidal composition for combatting Coleoptera, more specifically *Diabrotica* species.

4 Claims, No Drawings

METHOD OF CONTROLLING COLEOTERA USING *BACILLUS THURINGIENSIS* STRAINS MG P-14025 AND LMG P-14026

This application is a divisional of application Ser. No. 08/089,809, filed Jul. 12, 1993, now U.S. Pat. No. 5,369,027.

BACKGROUND OF THE INVENTION

1. Field of the Invention

The present invention relates to two new strains of *Bacillus thuringienses* (the "BTS02584B and BTS02584C strains") which produce crystal proteins (the "BTS02584B and BTS02584C crystal proteins") which are packaged in crystals (the "BTS02584B and BTS02584C crystals") during sporulation.

The present invention also relates to an insecticide composition that is active against Coleoptera, more particularly against *Diabrotica* species(hereinafter abbreviated "spp.") which comprises sporulated cultures of the BTS02584B or BTS02584C strains or the active component(s) thereof as an active insecticidal ingredient.

The present invention also relates to a method for combatting *Diabrotica* pests by contacting these pests with BTS02584B and/or BTS02584C strains, sporulated cultures of the BTS02584B and/or BTS02584C strains or with their insecticidally effective component(s).

2. Description of the Prior Art

Some of the most destructive pests are found among the Diabroticina beetles. In North America, the three important species of corn rootworms, *Diabrotica virgifera virgifera* (the Western corn rootworm), *Diabrotica barberi* (the Northern corn rootworm) and *Diabrotica undecimpunctata howardi* (the Southern corn rootworm) are considered to be the most expensive insect pests to control (Metcalf, 1986). *Diabrotica virgifera virgifera* and *Diabrotica barberi* are considered the most serious insect pests of corn in the major corn-producing states of the United States and Canada (Levine and Oloumi-Sadeghi 1991). The larvae feed on the roots and thus cause direct damage to corn growth and corn yields. Costs for soil insecticides to control larval damage to the root systems of corn and aerial sprays to reduce beetle damage to corn silks, when combined with crop losses, can approach one billion dollars annually (Metcalf, 1986).

*B. thuringienses* is a gram-positive bacterium which produces endogenous crystals upon sporulation. The crystals are composed of proteins which are specifically toxic against insect larvae. Three different Bt pathotypes have been described. Pathotype A that is active against Lepidoptera; pathotype B that is active against certain Diptera, e.g., mosquitoes and black flies; and pathotype C that is active against Coleoptera, e.g., beetles (Ellar et al., 1986). The fact that conventional submerged fermentation techniques can be used to produce Bt spores and sporulated cultures on a large scale makes Bt bacteria commercially attractive as a source of insecticidal compositions.

A Bt strain, whose crystals are toxic to Coleoptera, has been described as *Bt tenebrionis* and BTS1 in U.S. Pat. No. 4,766,203; European Patent Publication No. 0,213,818; U.S. Pat. No. 4,771,131; and European Patent Application No. 88/402,115.5. Subsequently, other Coleopteran-active strains have been isolated as described in PCT patent publications WO 91/00791 and WO 90/09445. The *Bt tenebrionis* strain which carries the Coleopteran-active *cryIIIa* gene has been reported to kill a variety of Coleoptera. However, according to Slaney et al (1992) the toxin encoded by this gene was found to be much less effective to *Diabrotica* larvae than to the Colorado potato beetle, *Leptinotarsa decemlineata*. *Diabrotica* was found to have a poor ability to bind the CryIIIA toxin.

OBJECTS AND SUMMARY OF THE INVENTION

An object of the present invention is to provide two new Bt strains of pathotype C; i.e., the BTS02584B and BTS02584C strains and variants of these strains.

Yet another object of the present invention is to provide sporulated cultures of BTS02584B and BTS02584C which possess insecticidal activity and can therefore be formulated into insecticidal compositions against Coleoptera in general and especially against *Diabrotica* species, *Agelastica alni*, *Hypera postica*, *Hypera brunneipennis*, *Haltica tombacina*, *Anthonomus grandis*, *Tenebrio molitor*, *Triboleum castaneum*, *Dicladispa armigera*, *Trichispa serica*, *Oulema oryzae*, *Colaspis brunnea*, *Lissorhorptrus oryzophilus*, *Phyllotreta cruciferae*, *Phyllotreta striolata*, *Psylliodes punctulata*, *Entomoscelis americana*, *Meligethes aeneus*, *Ceutorynchus sp.*, *Psylliodes chrysocephala*, *Phyllotreta undulata*, *Leptinotarsa decemlineata* (Colorado potato beetle) and more preferably against *D. undecimpunctata undecimpunctata* (Western spotted cucumber beetle), *D. undecimpunctata howardi* (Southern corn rootworm), *D. barberi* (Northern corn rootworm) and *D. virgifera virgifera* (Western corn rootworm), which are major pests of economically important crops such as corn.

Yet another object of the present invention is to provide an insecticidal composition against Coleoptera and a method for controlling Coleoptera with the insecticidal composition by contacting insects with the insecticidal composition that comprises BTS02584B and/or BTS02584C strains, BTS02584B and/or BTS02584C sporulated cultures and/or the active insecticidal component(s).

DETAILED DESCRIPTION OF THE PREFERRED EMBODIMENTS OF THE INVENTION

As used herein the term variant means a strain which differs from other related strains in a specified or unspecified way but retains the same insecticidal activity as the related strain. Variants can be made by conventional means including mutation by ultraviolet light sources, by use of chemicals such as nitrosoguanidine and the like.

More specifically the present invention relates to two new strains of *Bacillus thuringiensis* with significant insecticidal activity against insects of the family Chrysomelidae, particularly *Diabrotica* and *Leptinotarsa* spp. such as the Colorado potato beetle, *Lepinotarsa decemlineata* and the Western corn rootworm, *Diabrotica virgifera virgifera*. Strains BTS02584B and BTS02584C are isolated from grain dust found in the Phillipines using the usual methods known in the art (Travers et al., 1987). These strains typically grow in elongated chains of bacterial cells that give the liquid culture medium a flocculent appearance. In these long strands, spores are readily recognized under the microscope as opaque oval bodies, while the crystals are recognized as dense bipyramidal bodies. Upon higher magnification, the crystals seem to be composed of two pyramidal bodies linked together in the bipyramidal crystal. The strains can be grown in any medium such as T-3 agar and the like, but it is preferable to grow the strains in C2 medium.

Insect bioassays show a marked insecticidal activity of both strains and variants thereof to *Leptinotarsa decemlineata* and *Diabrotica virgifera virgifera*, but show no insecticidal activity to Lepidoptera.

The insecticidal active component found in these strains of the present invention is heat labile, is not insecticidal towards Lepidoptera and preliminary evidence indicates that the component is larger than 10 kD. It is believed that the insecticidal active component is a protein or a polypeptide-like compound which is present in sporulated cultures of the Bt strain.

An insecticidal, particularly anti-Coleopteran, composition of the present invention can be formulated in a conventional manner using sporulated cultures of the BTS02584B and/or BTS02584C strains or their insecticidal component(s) as active ingredients with suitable carriers, diluents, emulsifiers, dispersants and/or attractants. The insecticidal composition can be formulated as a wettable powder, pellets, granules, dust or as a liquid formulation with aqueous or non-aqueous solvents as a foam, gel, suspension, concentrate and the like. The concentration of the BTS02584B and/or BTS02584C strains and/or their insecticidal components in a composition depends upon the nature of the formulation and its intended mode of use. Generally, an insecticide composition of the present invention can be used to protect a potato or corn field for about 2 to 4 weeks against Coleoptera after the composition is applied. For more extended protection (e.g., for an entire growing season), additional amounts of the composition should be applied periodically.

A method for controlling insects, particulalrly Coleoptera, in accordance with the present invention preferably comprises applying (e.g., spraying) to a locus (area) to be protected an insecticidally effective amount of the BTS02584B and/or BTS02584C strains or their insecticidally active components. The locus to be protected can include, for example, the habitat of the insect pests or growing vegetation or an area where vegetation is to be grown.

To obtain the insecticidal component(s) of the BTS02584B and BTS02584C strains, cells of the BTS02584B and BTS02584C strains can be grown in a conventional manner on a suitable culture medium and then lysed using conventional means such as enzymatic degradation, detergents or the like. The insecticidal component(s) can then be separated and purified by standard techniques such as chromatography, extraction, electrophoresis or the like. If the insecticidal component(s) is proven to be a polypeptide it can be purified and sequenced by conventional methods as described in European Patent Publication Nos. 193,259 and 458,819. After the sequence is isolated it can be placed into an appropriate vector system and recombinantly produced according to the methods described in *Molecular Cloning, A Laboratory Manual*, 2nd edition, Cold Spring Harbor Laboratory Press, (1989).

The BTS02584B and BTS02584C cells also can be harvested and then applied intact, either dead or alive, preferably dried, to the locus to be protected. In this regard, it is preferred that purified BTS02584B and/or BTS02584C strains (either dead or alive) be utilized. It is most preferable to use a cell mass that contains 90.0 to 99.9% purified BTS02584B and BTS02584C.

The BTS02584B and/or BTS02584C sporulated cultures or their insecticidal component(s) can be formulated in an insecticidal composition in a variety of ways using any number of conventional additives, wet or dry, depending upon the particular use. Additives may include, for example, wetting agents, detergents, stabilizers, adhering agents, spreading agents, extenders and the like. Examples of such compositions include pastes, dusting powders, wettable powders, granules, baits, aerosol compositions and the like. Other Bt cells, toxins and insecticidally effective toxin portions and other insecticides, fungicides, biocides, herbicides, fertilizers and the like can be utilized in the composition containing the BTS02584B and/or BTS02584C sporulated cultures or their insecticidal component(s) to provide advantages or benefits. Such an insecticidal composition can be prepared in a conventional manner and the amount of BTS02584B and/or BTS02584C cells and/or insecticidal component(s) employed depends upon a variety of factors such as the insect pest targeted, the composition used, the type of area to which the composition is to be applied and the prevailing weather conditions. Furthermore, BTS02584B or BTS02584C sporulated cultures may be used separately or can be mixed together to form the active ingredient of the insecticidal composition. Generally, the concentration of BTS02584B or BTS02584C insecticidal component(s) is at least about 0.1% by weight of the formulation to about 100% by weight of the formulation and preferably from about 0.15% to about 0.8% of the formulation. Specifically for corn rootworm, application is preferably made to the roots.

In practice, some insects can be fed the BTS02584B and/or BTS02584C sporulated cultures, their insecticidally effective component(s) or mixtures thereof in the protected area; that is in the area where sporulated cultures or insecticidally effective component(s) have been applied. Alternatively, some insects can be fed intact live cells of the BTS02584B and/or BTS02584C strains or variants thereof, so that the insects ingest the insecticidal component(s) of these strains and suffer death or severe damage.

In order to further illustrate the present invention and advantages thereof, the following specific examples are given, it being understood that the same are intended only as illustrative and in nowise limitative.

Example 1: Characterization of the BTS02584B and BTS02584C strains

The BTS02584B and BTS02584C strains were deposited under the provisions of the Budapest Treaty on Jun. 14, 1993 at the Belgian Coordinated Collections of Microorganisms—Collection Laboratorium voor Microbiologie Belgium ("BCCM-LMG"), University of Gent, K. Ledeganckstraat 35, B-9000 Gent, Belgium. BTS02584B was deposited under accession number LMG P-14025, BTS02584C under accession number LMG P-14026.

The BTS02584B and BTS02584C strains were cultivated at 28° C. on C2 medium (containing: 10 g/l glucose, 5 g/l casamino acid, 2 g/l peptone, 2 g/l yeast extract, 0.247 g/l $MgCl_2.6H_2O$; 0.058 g/l $MnCl_2.4H_2O$; 0.1 g/l $CaCl_2$; 0.005 g/l $ZnSO_4.7H_2O$; 0.005 g/l $CuSO_4.7H_2O$; 1.619 g/l $NH_4Cl$; 0.0005 g/l $FeSO_4.7H_2O$; after autoclaving the following was added: 3.11 g/l $KH_2PO_4$ and 4.66 g/l $K_2HPO_4$). For long term storage, an equal volume of a spore crystal suspension with an equal volume of 50% glycerol was mixed and stored at −70° C. or lyophilized as a spore suspension. For sporulation, the use of liquid C2 medium was utilized for 72 hours at 28° C., followed by storage at 4° C. During their vegetative phase, the BTS02584B and BTS02584C strains can also grow under facultative anaerobic conditions, but sporulation only occurs under aerobic conditions.

After cultivating on C2 Agar ("CA", C2 medium containing 2% Agar, Difco Laboratories, Detroit, Mich., USA) for one day, colonies of the BTS02584B and BTS02584C strains formed opaque white colonies with irregular edges. Cells of the strains sporulated after three days cultivation at 28° C. on CA. The crystal proteins produced during sporulation were packed in crystals in the BTS02584B and BTS02584C strains. Furthermore, these strains typically grew in elongated chains of bacterial cells that gave the liquid culture medium a flocculent appearance. In these long strands, spores were readily recognized under the microscope as opaque oval bodies, while the crystals were recognized as dense bipyramidal bodies. Upon higher magnification, the crystals seemed to be composed of two pyramidal bodies linked together in the bipyramidal crystal.

Moreover, possibly because of this auto-agglutination, the Bt serotype could not be determined on the BTS02584B and BTS02584C strains by conventional serotyping methods as conducted by the WHO Collaborating Center for Entomopathogenic *Bacillus* (M. Lecadet).

Example 2: Characteristics of the BTS02584B and BTS02584C insect icidal component(s)

The BTS02584B and BTS02584C strains were grown for 72 hours at 28° C. on C2 medium. After sporulation, the sporulated cultures were harvested by centrifugation to pellet the cells and the spores and were then suspended in a tap water-Triton X-100 solution (75 μl TX-100 per 200 ml tap water; TX-100 from Sigma, St. Louis, USA), that is non-toxic to *Diabrotica*. The suspensions of these sporulated cultures were tested against coleopteran and lepidopteran insects and were found to be highly and specifically toxic for the tested Coleoptera. Furthermore, the insecticidal component(s) in these suspensions was tested for heat inactivation for 10 min. at 95° C. The results of the heat inactivation test are set forth in Table 1. The specificity of the activity and the thermolability are strong indications of the proteinaceous nature of the BTS02584B and BTS02584C insecticidal component(s).

Dialysis of the suspension of sporulated cultures of Bt strain BTS02584B indicated that the insecticidal component had a molecular weight of over 10 kD. The insecticidal activity was retained after prolonged dialysis using membranes having a molecular weight cut-off point of about 10 kD. This is another indication of the proteinaceous nature of the component.

Example 3: Insecticidal activity of the BTS02584B and BTS02584C strains

The BTS02584B and BTS02584C strains were grown for 72 hours at 28° C. on C2 medium. After sporulation, the sporulated cultures were harvested in a tap water-Triton X-100 solution (75 μl TX-100 per 200 ml tap water; TX-100 from Sigma, St. Louis, USA) that is non-toxic to *Diabrotica*. The suspensions of these sporulated cultures were tested against *Diabrotica virgifera, Leptinotarsa decemlineata* and some selected Lepidoptera.

For *Diabrotica virgifera v.* assays, pieces of corn leaves of one week old plants (size: 1 cm$^2$) were dipped in a suspension of sporulated BTS02584B or BTS02584C cultures and were dried in a laminar flow cupboard. When dry, the leaflets were placed on agar (2%) in 24 multiwell plates. On each leaflet 4 neonate *Diabrotica virgifera virgifera* larvae were placed; 24 larvae were used per bioassay. After 2 days the leaflets were removed and fresh corn leaves were placed in the wells. After four days the dead and living larvae were counted. The results on *D. virgifera virgifera* are shown in Table 1.

For *Leptinotarsa decemlineata* assays, potato leaves were dipped either in a suspension of sporulated BTS02584B or BTS02584C cultures and then air dried for two hours. Colorado potato beetle larvae of the first instar were placed on the treated leaves, and mortality of the larvae was determined after three days. These results were compared with the mortality of larvae fed leaves treated with spore-crystal mixtures of BTS1 (*B. thuringiensis* BTS1 from DSM accession no 4288) which was used as a reference strain. The results obtained with the Colorado potato beetle larvae are shown in Table 2.

The assays showed that the suspension of the BTS02584B and BTS02584C sporulated cultures caused *Diabrotica* and *Leptinotarsa* larvae to stop feeding after about one day and die within a few days. In addition, Table 1 shows that boiling the suspension for 10 minutes resulted in a significant decrease in insecticidal activity towards *D. virgifera*. This indicates that the insecticidally effective compound is heat-labile.

Furthermore, suspensions of sporulated cultures of both strains BTS02584B and BTS02584C were shown to have no toxicity towards the tested Lepidoptera of *Plutella xylostella, Heliothis virescens* and *Spodoptera littoralis* which were not killed and developed normally. These Lepidoptera were tested in diet application assays. Artificial diet was dispensed in wells of Costar 24-well plates. 50 μl of a sample dilution (in phosphate buffered saline—Bovine serum albumin buffer containing per liter of distilled water: 8.7 g NaCl, 22.5 g Na$_2$H- PO$_4$.2H$_2$O, 2 g KH$_2$PO$_4$, 0.1% BSA) was applied on the surface of the diet and dried in a laminar air flow. Two larvae were placed in each well used per sample dilution (neonate larvae were used, except for *Plutella* in which third instar larvae were used). These data show the specificity of the BTS02584B and BTS02584C insecticidal component(s) towards Coleoptera, and more specifically to *Diabrotica* and *Leptinotarsa*.

Example 4: Further Insecticidal activity of the BTS02584B and S02584C strains Following the procedure set forth in Example 3, BTS02584B and BTS02584C strains are used to test the insecticidal activity on the following insect pests:

*Diabrotica undecimpunctata undecimpunctata, Diabrotica undecimpunctata howardi, Diabrotica barberi, Agelastica alni, Hypera brunneipennis, Hypera postica, Haltica tombacina, Anthonomus grandis, Tenebrio molitor, Triboleum castaneum, Dicladispa armigera, Trichispa serica, Oulema oryzae, Colaspis brunnea, Lissorhorptrus oryzophilus, Phyllotreta cruciferae, Phyllotreta striolata, Psylliodes punctulata, Entomoscelis americana, Meligethes aeneus, Ceutorynchus species, Psylliodes chrysocephala* and *Phyllotreta undulata.*

Similar results are obtained as indicated in Tables 1 and 2.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

TABLE 1

| Diabrotica virgifera virgifera Larvae | | | |
|---|---|---|---|
| Strain | Experiment Number | Concentration Spores-crystal/ml | Mortality |
| BTS0258B | 1 | >$10^9$ | 71% |
| Control (Triton-water) | 1 | 0 | 12% |
| BTS0258B | 2 | $4.4 \times 10^9$ | 96% |
|  |  | $4.4 \times 10^9$ | 88% |
|  |  | $10^9$ | 88% |
|  |  | $10^9$ | 92% |
| Control | 2 | 0 | 0 |
| BTS02584B | 3 | $3.4 \times 10^9$ | 96% |
|  |  | $3.4 \times 10^9$ | 92% |
|  |  | $10^9$ | 79% |
|  |  | $10^9$ | 92% |
| BTS02584C | 3 | $3.4 \times 10^9$ | 88% |
|  |  | $10^9$ | 79% |
| Control | 3 | 0 | 4% |
| BTS02854B | 4 | $10^9$ | 79% |
|  |  | $10^9$ | 83% |
|  |  | $10^9$ | 83% |
| BTS02584C | 4 | $10^9$ | 100% |
|  |  | $10^9$ | 88% |
|  |  | $10^9$ | 79% |
|  |  | $10^9$ | 100% |
| Control | 4 | 0 | 4% |
| BTS02584B | 5 | $10^9$ | 88% |
|  |  | $10^9$ | 92% |
|  |  | $10^9$ | 92% |
| BTS02584B (boiled) | 5 | $10^9$ | 33% |
|  |  | $10^9$ | 21% |
|  |  | $10^9$ | 54% |
| Control | 5 | 0 | 8% |

TABLE 2

| Leptinotarsa decemlineata larvae | | | |
|---|---|---|---|
| Strain | Experiment Number | Concentration Spores-crystal/ml | Mortality |
| BTS02584B | 1 | $10^9$ | 87% |
| BTS1[a] | 1 | $10^9$ | 100% |
| Control (buffer) | 1 | 0 | 6% |
| BTS02584C | 2 | $10^9$ | 100% |
|  |  | $10^9$ | 100% |
| BTS1[a] | 2 | $10^9$ | 100% |
|  |  | $10^9$ | 100% |
| Control | 2 | 0 | 0 |

[a] Leptinotarsa-active BTS1 strain of DSM accession number 4288

References

Ellar et al, in "Fundamental and Applied aspects of Invertebrate Pathology", ed. Samson, R. A., Vlak, J. M. and Peters, D., pp. 7–10, Wageningen, Foundation of the fourth International Colloquim of Invertebrate Pathology, 1986.

Levine and Oloumi-Sadeghi, Annu. Rev. Entomol. 36, 229–55, 1991.

Metcalf, R. L., Foreword in "Methods for the Study of Pest Diabrotica", pp. vii–xv, eds. Krysan, J. L. and Miller, T. A., Springer-Verlag, New York, 1986.

Slaney, A. C. et al, Insect Biochem. Molec. Biol. 22, 9–18, 1992.

Travers et al., Applied & Environmental Microbiology., vol. 53, 1263–1266, 1987.

What is claimed is:

1. An insecticidal composition comprising an active ingredient selected from the group consisting of *Bacillus thuringiensis* LMG P-14025, *Bacillus thuringiensis* LMG P-14026 and sporulated cultures of the two strains, and an agriculturally acceptable carrier.

2. The insecticidal composition of claim 1, wherein said composition is active against Coleoptera.

3. A process for controlling an insect pest, said pest being selected from the group of *Diabrotica undecimpunctata undecimpunctata, Diabrotica undecimpunctata howardi, Diabrotica barberi, Diabrotica virgifera virgifera, Leptinotarsa decemlineata, Agelastica alni, Hypera brunneipennis, Hypera postica, Haltica tombacina, Anthonomus grandis, Tenebrio molitor, Triboleum castaneum, Dicladispa armigera, Trichispa serica, Oulema oryzae, Colaspis brunnea, Lissorhorptrus oryzophilus, Phyllotreta cruciferae, Phyllotreta striolata, Psylliodes punctulata, Entomoscelis americana, Meligethes aeneus, Ceutorynchus* species, *Psylliodes chrysocephala* and *Phyllotreta undulata* comprising contacting said pest with an insecticidal composition comprising an active ingredient selected from the group consisting of *Bacillus thuringiensis* LMG P-14025, *Bacillus thuringiensis* LMG P-14026 and sporulated cultures of the two strains, and an agriculturally acceptable, carrier.

4. The process according to claim 3, wherein said insect pest is *Diabrotica virgifera virgifera* or *Leptinotarsa decemlineata*.

* * * * *

UNITED STATES PATENT AND TRADEMARK OFFICE
CERTIFICATE OF CORRECTION

PATENT NO. : 5,422,106
DATED : June 6, 1995
INVENTOR(S) : Bart J. LAMBERT et al

It is certified that error appears in the above-indentified patent and that said Letters Patent is hereby corrected as shown below:

On the title page:

Item [54] and col. 1, at line 1, please delete "Coleotera" and insert therefor --Coleoptera--; and at line 3, please delete "MG" and insert therefor --LMG--.

Signed and Sealed this

Twenty-first Day of May, 1996

Attest:

BRUCE LEHMAN

Attesting Officer     Commissioner of Patents and Trademarks